US010566087B1

(12) United States Patent
Puckett

(10) Patent No.: US 10,566,087 B1
(45) Date of Patent: Feb. 18, 2020

(54) OPTIMIZED DRUG SUPPLY LOGISTICAL TECHNIQUES

(71) Applicant: Verity Solutions, Kirkland, WA (US)

(72) Inventor: George Puckett, Kirkland, WA (US)

(73) Assignee: Verity Solutions, Kirkland, WA (US)

(*) Notice: Subject to any disclaimer, the term of this patent is extended or adjusted under 35 U.S.C. 154(b) by 0 days.

(21) Appl. No.: 16/178,447

(22) Filed: Nov. 1, 2018

Related U.S. Application Data

(60) Provisional application No. 62/715,208, filed on Aug. 6, 2018.

(51) Int. Cl.
  G16H 40/20 (2018.01)
  G06Q 10/08 (2012.01)

(52) U.S. Cl.
  CPC ........... G16H 40/20 (2018.01); G06Q 10/087 (2013.01)

(58) Field of Classification Search
  CPC ..................... G16H 40/20; G06Q 10/087
  See application file for complete search history.

(56) References Cited

U.S. PATENT DOCUMENTS

| 2004/0230502 | A1 | 11/2004 | Fiacco et al. |
| 2009/0254412 | A1 | 10/2009 | Braswell et al. |
| 2011/0251850 | A1 | 10/2011 | Stephens |
| 2012/0030070 | A1 | 2/2012 | Keller et al. |
| 2014/0148945 | A1* | 5/2014 | Cunningham .......... G07F 9/026 700/236 |
| 2015/0278924 | A1* | 10/2015 | Maurer .............. G06Q 30/0635 705/26.81 |
| 2015/0332422 | A1 | 11/2015 | Gilmartin |
| 2016/0042147 | A1 | 2/2016 | Maurer et al. |

OTHER PUBLICATIONS

Karralli et al., Development of a metrics dashboard for monitoring involvement in the 340B Drug Pricing Program, Sep, 1, 2015, Am J Health-Syst Pharm, vol. 72, pp. 1489-1495. (Year: 2015).*

* cited by examiner

Primary Examiner — Christopher L Gilligan
(74) Attorney, Agent, or Firm — Perkins Coie LLP

(57) ABSTRACT

A facility for ordering drugs is described. For each of a number of different drugs, the facility maintains a single outpatient counter of administrations of the drug to outpatients that have not been used as a basis for reordering the drug. For a distinguished one of the drugs, based on the value of the counter of administrations of the distinguished drug, the facility places an order that reorders the distinguished drug at a discounted outpatient price level.

21 Claims, 12 Drawing Sheets drug price schedule 300

| drug | seller | container size | price level | price per dose | |
|---|---|---|---|---|---|
| Amoxicillin | A | 50 | GPO | $5.85 | 311 |
| Amoxicillin | A | 50 | WAC | $11.50 | 312 |
| Amoxicillin | A | 50 | 340B | $4.90 | 313 |
| Amoxicillin | B | 50 | GPO | $6.90 | 314 |
| Amoxicillin | B | 50 | WAC | $12.10 | 315 |
| Amoxicillin | B | 50 | 340B | $5.20 | 316 |
| Amoxicillin | C | 50 | GPO | $7.15 | 317 |
| Amoxicillin | C | 50 | WAC | $13.15 | 318 |
| Amoxicillin | C | 50 | 340B | $6.60 | 319 |
| Amoxicillin | A | 100 | GPO | $6.85 | 320 |
| ... | | | | | |
| Ibuprofen | A | 50 | GPO | $1.50 | 321 |
| ... | | | | | |

301  302  303  304  305

*FIG. 3* dispense table 400

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | |
| 10/10/2019 | 16:19:21 | 331A | 111-55-8888 | inpatient | Amoxicillin | |
| 10/10/2019 | 22:01:33 | 222C | 777-33-9999 | outpatient | Amoxicillin | |
| 10/10/2019 | 22:12:22 | 301A | 111-55-8888 | inpatient | Amoxicillin | |
| ... | | | | | | |

| unapplied dispense tally table 500 | | |
|---|---|---|
| drug | inpatient or outpatient | count of unapplied dispenses |
| Amoxicillin | inpatient | 63 — 511 |
| Amoxicillin | outpatient | 44 — 512 |
| Ibuprofen | inpatient | 7 — 513 |
| ... | | |

FIG. 6 drug purchase table — 600

| purchase ID | date | price level | drug | seller | container size |
|---|---|---|---|---|---|
| 983991 | 4/4/2017 | WAC | Amoxicillin B | | 50 |

601, 602, 603, 604, 605, 606, 611

FIG. 7 drug purchase table — 700

| purchase ID | date | price level | drug | seller | container size |
|---|---|---|---|---|---|
| 983991 | 4/4/2017 | WAC | Amoxicillin B | | 50 |
| 991001 | 10/11/2019 | GPO | Amoxicillin A | | 50 |

701, 702, 703, 704, 705, 706, 711, 712

FIG. 8 dispense table — 800

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | |
| 10/10/2019 | 16:19:21 | 331A | 111-55-8888 | inpatient | Amoxicillin | 991001 |
| 10/10/2019 | 22:01:33 | 222C | 777-33-9999 | outpatient | Amoxicillin | |
| 10/10/2019 | 22:12:22 | 301A | 111-55-8888 | inpatient | Amoxicillin | 991001 |
| ... | | | | | | |

801  802  803  804  805  806  807

811  812  813  814  815  816 unapplied dispense tally table — 900

| drug | inpatient or outpatient | count of unapplied dispenses |
|---|---|---|
| Amoxicillin | inpatient | 13 |
| Amoxicillin | outpatient | 44 |
| Ibuprofen | inpatient | 7 |
| ... | | |

*FIG. 9*

FIG. 10 dispense table — 1000

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | |
| 10/10/2019 | 16:19:21 | 331A | 111-55-8888 | inpatient | Amoxicillin | |
| 10/10/2019 | 22:01:33 | 222C | 777-33-9999 | outpatient | Amoxicillin | 991001 |
| 10/10/2019 | 22:12:22 | 301A | 111-55-8888 | inpatient | Amoxicillin | |
| 10/11/2019 | 5:11:12 | 301A | 111-55-8888 | inpatient | Amoxicillin | 991001 |
| 10/11/2019 | 5:31:02 | 110 | 888-00-1111 | outpatient | Amoxicillin | |
| ... | | | | | | |

| drug | inpatient or outpatient | count of unapplied dispenses |
|---|---|---|
| Amoxicillin | inpatient | 51 |
| Amoxicillin | outpatient | 60 |
| Ibuprofen | inpatient | 21 |
| ... | | | unapplied dispense tally table — 1100

FIG. 12

| purchase ID | date | price level | drug | seller | container size |
|---|---|---|---|---|---|
| 983991 | 4/4/2017 | WAC | Amoxicillin | B | 50 |
| 991001 | 10/11/2019 | GPO | Amoxicillin | A | 50 |
| 991340 | 10/12/2019 | 340B | Amoxicillin | B | 50 | drug purchase table — 1200

FIG. 13 dispense table — 1300

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | 991340 |
| 10/10/2019 | 16:19:21 | 331A | 111-55-8888 | inpatient | Amoxicillin | 991001 |
| 10/10/2019 | 22:01:33 | 222C | 777-33-9999 | outpatient | Amoxicillin | 991340 |
| 10/10/2019 | 22:12:22 | 301A | 111-55-8888 | inpatient | Amoxicillin | 991001 |
| 10/11/2019 | 5:11:12 | 301A | 111-55-8888 | inpatient | Amoxicillin | |
| 10/11/2019 | 5:31:02 | 110 | 888-00-1111 | outpatient | Amoxicillin | 991340 |
| ... | | | | | | |

| drug | inpatient or outpatient | count of unapplied dispenses |
|---|---|---|
| Amoxicillin | inpatient | 51 |
| Amoxicillin | outpatient | 10 |
| Ibuprofen | inpatient | 21 |
| ... | | | unapplied dispense tally table 1400

1401, 1402, 1403

1411, 1412, 1413

OPTIMIZED DRUG SUPPLY LOGISTICAL TECHNIQUES

CROSS-REFERENCE TO RELATED APPLICATION

This application claims the benefit of U.S. Provisional Application No. 62/715,208, filed on Aug. 6, 2018, which is hereby incorporated by reference in its entirety. In cases in which a document incorporated by reference herein is inconsistent with contents of this application, the contents of this application control.

BACKGROUND

Hospitals and other kinds of healthcare facilities dispense drugs to patients. The healthcare facilities generally purchase these drugs from suppliers.

BRIEF DESCRIPTION OF THE DRAWINGS

FIGS. 3-14 are data structure diagrams showing sample contents of tables used by the facility in some embodiments.

DETAILED DESCRIPTION

Figure 1:
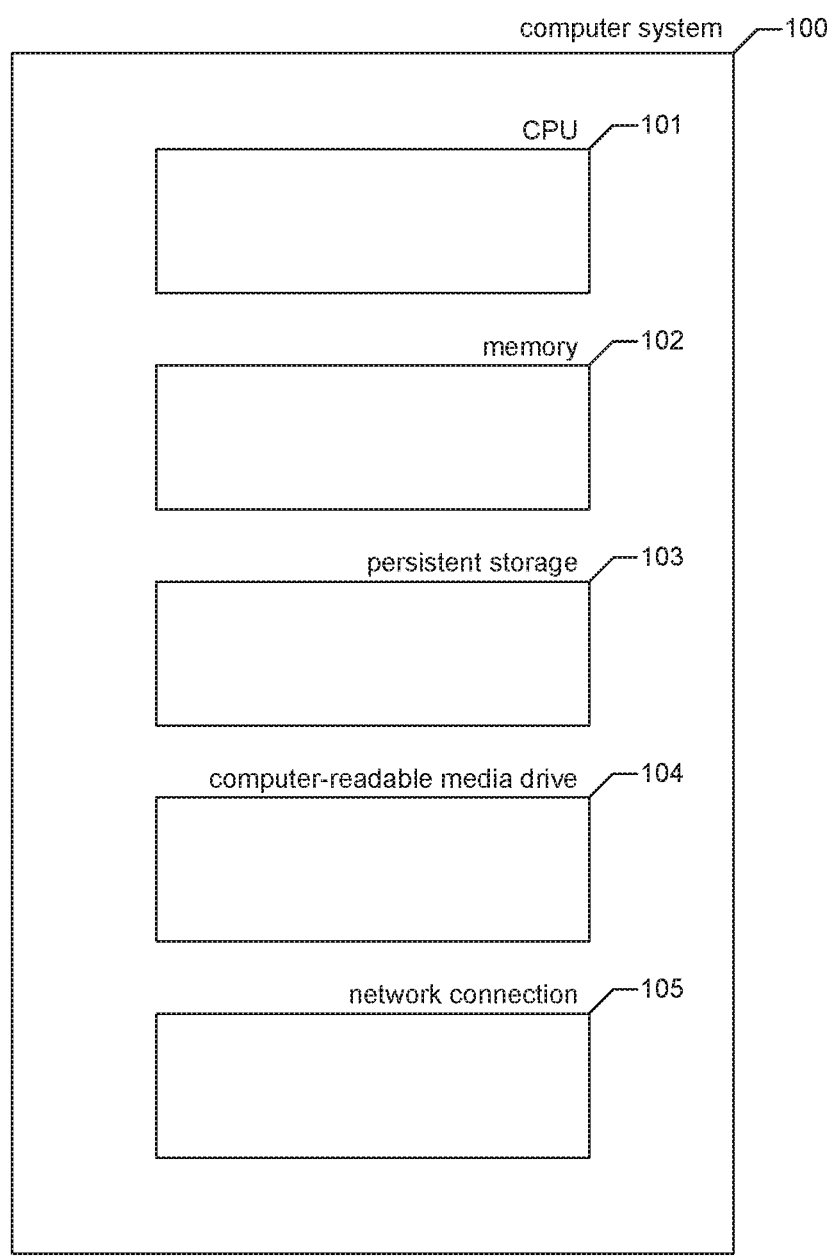
FIG. 1 is a block diagram showing some of the components typically incorporated in at least some of the computer systems and other devices on which the facility operates.

Section 340B of the Public Health Service Act provides a discounted drug pricing program that applies to certain purchases of drugs by certain healthcare facilities ("enrolled entities"). For efficiency's sake, enrolled entity healthcare facilities of all types are sometimes referred to herein as "hospitals."

Under section 340B, an enrolled entity must order drugs separately for patients treated as inpatients and patients treated as outpatients. For patients treated as inpatients, the enrolled entity typically always orders at a discounted price for inpatients, called "GPO" (Group Purchasing Organization price). For patients treated as outpatients, the enrolled entity first orders a particular drug from a particular seller at a retail price called "WAC" (Wholesale Acquisition Cost). The enrolled entity can subsequently REORDER the same drug from the same seller at a discounted 340B price. In order to perform this reorder of a container of drugs at 340B price, the enrolled entity must be able to show that (1) it previously purchased the same-sized container from the same seller at WAC; and (2) it has dispensed all of the doses contained by a container of that size to inpatients. At enrolled entities that commingle drugs they purchase for inpatients at GPO with drugs they purchase for outpatients at WAC and 340B price, any meaningful attempt at 340B compliance must involve strict accounting for drugs dispensed to inpatients versus outpatients.

To satisfy the requirement that an enrolled entity be able to, for a container of a drug reordered at 340B price, account for the dispenses of all of the doses in the container to outpatients, conventional compliance systems attribute each administration of a dose of a drug (a "dispense") to an inpatient as soon as it occurs to a particular combination of the drug with a container size and a seller from whom the drug was purchased in that container size. When a hospital seeks to order a drug in a particular container size from a particular seller, conventional systems count the doses dispensed to outpatients attributed to the combination of the drug, container size, and seller, to see if they add up to the number of doses in the container size; only if they do does a conventional system allow the purchase to proceed as a reorder at 340B price; otherwise, a conventional system performs the order at the more expensive WAC price.

The inventors have recognized a number of disadvantages with the approach employed by conventional systems. First, for any given dispensed dose, it can be difficult to identify the combination of container size and seller to which to attribute the dispense, costing the conventional system significant processing resources. Second, in some cases, the complex logic needed to attribute a dispense to a combination of container size and seller may fail, depriving the healthcare facility of any pricing benefit from the outpatient dispense. Third, the conventional approach often unnecessarily extends the healthcare facility's purchase of drugs at higher WAC prices that could instead be purchased at lower 340B prices.

In order to overcome these disadvantages of conventional systems, the inventors have conceived and reduced to practice a software and/or hardware facility for ordering drugs using late attribution and price optimization ("the facility").

The facility responds to a dispense to an inpatient by incrementing a counter not associated with any particular container size or seller, but only with the drug. At the time of ordering a new container of a drug of a particular size from a particular seller, the facility checks to see (1) whether the hospital previously ordered a container of that drug of that size from the same seller, and (2) whether the number of dispensed doses in this much broader counter is as least as great as the number that fits in the container. If so, the facility allows the drug to be ordered at 340B price, only then attributing a set of unattributed outpatient dispenses whose number matches the size of the container to the order, which has a particular combination of container size and seller.

In some embodiments, rather than specifying the seller from which it wants to buy a drug, the hospital simply specifies the drug and container size it wants. The facility automatically identifies a seller to order it from based upon (a) current price schedules from all sellers at all price levels, (b) the sellers from which containers of the drug have been previously purchased, and (c) the number of doses of the drug dispensed to inpatients that haven't already been used as the basis for a 340B order.

In some embodiments, the hospital specifies the drug and number of doses it wants, to the exclusion of container size. In response, the facility automatically chooses both seller and container size(s) in a way that optimizes average price paid per dose.

By performing in some or all of the ways described above, the facility (1) simplifies the process of dispense attribution, such that it consumes lower levels of processing and storage resources, permitting it to be executed on less powerful and less expensive hardware resources and/or permitting it to execute using lower levels of cloud computing and storage resources; (2) does not discard the pricing benefit of any outpatient dispense; and/or (3) on average accelerates the opportunity to purchase drugs at lower 340B prices.

FIG. 1 is a block diagram showing some of the components typically incorporated in at least some of the computer systems and other devices on which the facility operates. In various embodiments, these computer systems and other devices 100 can include server computer systems, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 101 for executing computer programs; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 2:
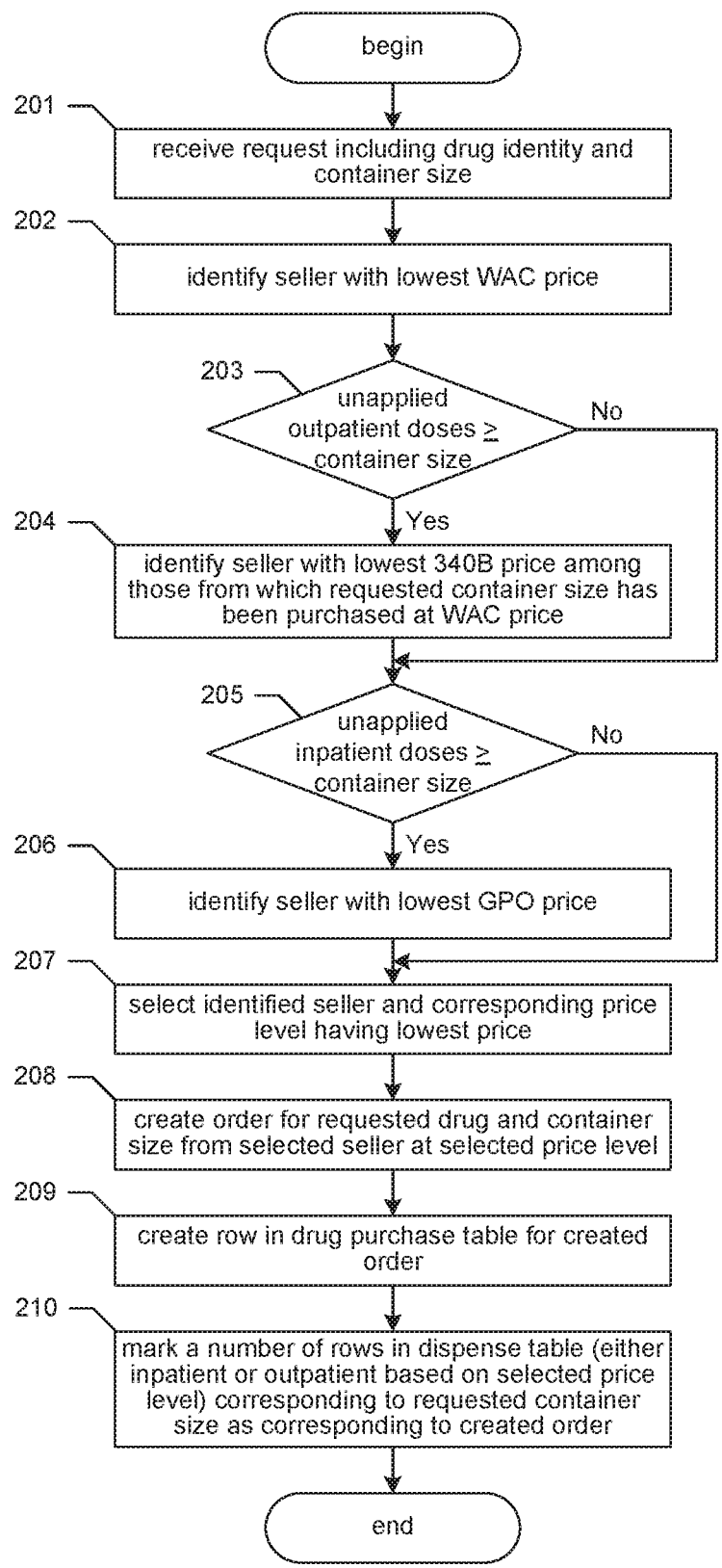
FIG. 2 is a flow diagram showing a process performed by the facility in some embodiments in order to handle a drug ordering request.

FIG. 2 is a flow diagram showing a process performed by the facility in some embodiments in order to handle a drug ordering request on behalf of a subject hospital. In act 201, the facility receives a request that includes the identity of a drug to be ordered on behalf of a subject hospital and a container size. In various embodiments, the request identifies the drug in one or more various ways, including: chemical identity; form, such as tablet, capsule, drink, injection, aerosol, etc.; manufacturer and/or brand-name; and/or encoded identifiers conveying this or other information. In an example, the facility receives a first request to purchase a 50-dose container of the drug Amoxicillin. In act 202, the facility identifies the seller having the lowest WAC price. FIG. 3 is a table diagram showing sample contents of a drug price schedule table. The drug price schedule table 300 contains current pricing information for drugs available from different sellers at different price levels. In various embodiments, the drug price schedule table is updated at regular intervals; in response to notifications from sellers; in response to each attempt to read it; etc. Each row of the drug price schedule table 300, such as shown rows 311-321, corresponds to a different combination of a drug, a seller, a container size, and a price level. Each row is divided into the following columns: a drug column 301 identifying the drug to which the row corresponds; a seller column 302 identifying a seller to whom the row corresponds; a container size column 303 showing the number of doses contained by a container to which the row corresponds; a price level column 304 identifying the pricing program to which the row corresponds; and a price per dose column 305 indicating the price per dose to order the drug from the seller in the specified container size at the specified price level. For example, row 311 indicates that the drug Amoxicillin can be ordered from seller A in a container holding 50 doses at the GPO price level for $5.85 a dose.

While FIG. 3 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed and/or encrypted; may contain a much larger number of rows than shown; etc.

The drug price schedule 300 shown in FIG. 3 contains WAC prices for Amoxicillin in rows 312, 315, and 318. By comparing these, the facility determines that the lowest WAC price is $11.50 for seller A shown in row 312. Accordingly, in act 203, the facility identifies seller A.

In act 203, if the number of unapplied outpatient doses of this drug is greater than or equal to the requested container size, then the facility continues in act 204, else the facility continues in act 205. In some embodiments, the facility performs the comparison of act 203 using contents of a dispense table and/or an unapplied dispense tally table, shown in FIGS. 4 and 5 and discussed below.

FIG. 4 is a table diagram showing sample contents of a dispense table at a first time. The dispense table 400 is made up of rows, such as shown rows 411-416, each corresponding to an instance in which a dose of a drug was administered to a patient by the subject hospital. Each row is divided into the following columns: a date column 401 indicating the date on which the drug was dispensed; a time column 402 indicating a time at which the drug was dispensed; a location column 403 indicating a physical location at which the drug was dispensed; a patient column 404 containing an identifier of the patient to whom the drug was dispensed; an inpatient or outpatient column 405 indicating whether the drug was dispensed to the patient as an inpatient or as an outpatient; a drug column 406 identifying the dispensed drug; and a purchase ID of purchase to which applied column 407, identifying a purchase of the dispensed drug that occurred after the dispense that was made to replace the dose of the drug given to the patient in the dispense to which the row corresponds. For example, row 411 indicates that, at 3:54:03 PM on Oct. 10, 2019, a patient having the identifier 44-11-3333 was given the drug Amoxicillin in location 407A as an outpatient, and that this dispense was later used as a basis for repurchasing Amoxicillin in a purchase having purchase ID 983991.

In some embodiments, the comparison of act 203 is performed based upon a query performed against the dispense table that counts the number of rows of the dispense table having "outpatient" in the inpatient or outpatient column 405, having "Amoxicillin" in the drug column 406, and having no purchase ID in the purchase ID of purchase to which applied column 407. Across rows 411-416 of dispense table 400 shown in FIG. 4, this query would return the result "2"; across all of the rows of dispense table 400, including those not shown in FIG. 4, the result may be larger.

FIG. 5 is a table diagram showing sample contents of an unapplied dispense tally table at the first time. The unapplied dispense tally table is based on the dispense table and summarizes the dispense table in a way that is useful in performing act 203. In various embodiments, the unapplied dispense tally table is updated in response to each change to the dispense table; re-created from the dispense table at regular intervals; re-created from the dispense table in response to each attempt to read the unapplied dispense tally table; etc.

The unapplied dispense tally table 500 is made up of rows, such as shown rows 511-513, each corresponding to a different combination of drug with inpatient or outpatient patient status. Each row is divided into the following columns: a drug column 501 identifying a drug that has been dispensed by the subject hospital; an inpatient or outpatient column 502 indicating whether the row is included in the unapplied dispense tally table to count dispenses to inpatients or dispenses to outpatients; and a count of unapplied dispenses column 503 indicating the number of dispenses of the drug to which the row corresponds that have been performed to patients having the status to which the row corresponds and have not been used as a basis for reordering that drug. For example, row 511 indicates that 63 doses of Amoxicillin have been administered to inpatients and not subsequently used as a basis for reordering Amoxicillin.

In the example represented by the contents of the dispense table and unapplied dispense tally table shown in FIGS. 4 and 5, only 44 doses of Amoxicillin have been administered to outpatients and not used as a basis to reorder Amoxicillin (see row 412 of unapplied dispense tally table 500), which is less than the 50-dose container size specified by the first purchase request. Accordingly, the facility continues in act 205.

Returning to FIG. 2, in act 205, if the number of unapplied inpatient doses is greater than or equal to the requested container size, then the facility continues in act 206, else the facility continues in act 207. In a manner similar to that described above in connection with act 203, the facility performs the comparison of act 205 based on the contents of the dispense table and/or the unapplied dispense tally table. In this case, 63 doses of Amoxicillin have been administered to inpatients and not used as a basis to reorder Amoxicillin (see row 511 of unapplied dispense tally table 500), which is greater than or equal to the 50-dose container size specified by the first purchase request. Accordingly, the facility continues in act 206.

In act 206, the facility identifies the seller having the lowest GPO price. In some embodiments, the facility uses a drug price schedule table to perform the identification of act 206. By comparing the contents of the price per dose column for rows 311, 314, and 317 of drug price schedule table 300, the facility identifies seller as having the lowest GPO price for Amoxicillin in a 50-dose container.

Returning to FIG. 2, in act 207, the facility selects the identified seller and identified the corresponding price level having the lowest price. For the first purchase request, two combinations of seller and price level are identified: (1) seller A and the WAC price level $11.50 identified in act 202, and (2) seller A and the GPO price level $5.85 identified in act 206. In act 207, the facility selects the lower of these, seller A and the GPO price level. In act 208, the facility creates an order for the requested drug, here Amoxicillin, and requested container size, here 50 doses, from the selected seller, seller A, at the selected price level, the GPO price level. In various embodiments, the facility communicates the order to the seller in a variety of ways, such as by calling an API exposed by the seller; sending an email or fax to the seller; automatically interacting with a web interface exposed by the seller; etc. In act 209, the facility creates a row in a drug purchase table for the created order.

FIGS. 6-7 show the creation of a row in the drug purchase table for the created order. FIG. 6 is a table diagram showing sample contents of the drug purchase table at the first time. The drug purchase table 600 is made up of rows, such as shown row 611, each corresponding to a different purchase of a drug by the subject hospital. Each row is divided into the following columns: a purchase ID column 601 unique identifying the purchase; a date column 602 identifying the date on which the purchase occurred; a price level column 603 identifying the prep price level at which the purchase was made; a drug column 604 identifying the drug purchased; a seller column 605 identifying the seller from which the drug was purchased; and a container size column 606 indicating the size of the purchase container of the drug. For example, row 611 indicates that the purchase having purchase ID 983991 was performed on Apr. 4, 2017 from seller B, purchasing a 50-dose container of Amoxicillin at the WAC price level.

FIG. 7 is a table diagram showing sample contents of the drug purchase table at a second time later than the first time, after the drug purchase table has been updated in response to the purchase for the first request. By comparing drug purchase table 700 shown in FIG. 7 to drug purchase table 600 shown in FIG. 6, it can be seen that the facility has added row 712, which corresponds to the purchase for the first request. In particular, row 712 indicates that the purchase having purchase ID 991001 was performed on Oct. 11, 2019 from seller A, purchasing a 50-dose container of Amoxicillin at the GPO price level.

Returning to FIG. 2, in act 210, the facility marks a number of rows of the dispense table that corresponds to the requested container size as corresponding to the order created in act 208.

FIG. 8 is a table diagram showing sample contents of the dispense table at the second time, after it has been updated by the facility in act 210. By comparing dispense table 800 shown in FIG. 8 is dispense table 300 shown in FIG. 4, it can be seen that the facility has added purchase ID 991001 to rows 814 and 816, each corresponding to a dispense of the drug Amoxicillin to a patient as an inpatient. Act 210 also involves adding this purchase ID to 48 other rows each corresponding to a dispense of the drug Amoxicillin to a patient as an inpatient, not shown in FIG. 8.

In some embodiments, this modification to the dispense table automatically updates the unapplied dispense tally table to reduce the count of unapplied dispenses column for the appropriate row by the size of the purchase container. In some embodiments, the facility explicitly updates the unapplied dispense tally table to perform this reduction (not shown in FIG. 2).

FIG. 9 is a table diagram showing sample contents of the unapplied dispense tally table at the second time, after it has been updated to reflect changes to the dispense table based upon the purchase performed in response to the first request. By comparing unapplied dispense tally table 900 shown in FIG. 9 to unapplied dispense tally table 400 shown in FIG. 5, it can be seen that the facility has, in row 911, reduced the count of unapplied dispenses to inpatients of Amoxicillin by the size of the purchase container—50 doses—from 63 to 13.

Continuing the example, in a second purchase request received at a third time, the purchase of another 50-dose container of Amoxicillin is requested. FIGS. 10 and 11 show the contents of the dispense table and the unapplied dispense tally table at this third time when the second purchase request is received. By comparing the dispense table 1000 shown in FIG. 10 to dispense table 800 shown in FIG. 8, it can be seen that additional dispenses of the drug Amoxicillin have been performed, as shown for example in new rows 1017 and 1018 of dispense table 1000. By comparing the unapplied dispense tally table 1100 shown in FIG. 11 to unapplied dispense tally table 900 shown in FIG. 9, it can be seen that the count of unapplied inpatient dispenses of Amoxicillin is now 51, and the count of unapplied outpatient dispenses of Amoxicillin is now 60.

In performing the process shown in FIG. 2 for the second purchase request: In act 202, the facility identifies the seller having the lowest WAC price. The drug price schedule 500 shown in FIG. 3 contains WAC prices for Amoxicillin in rows 512, 515, and 518. By comparing these, the facility determines that the lowest WAC price is $11.50 for seller A shown in row 512. Accordingly, in act 203, the facility identifies seller A as having the lowest WAC price. (While in some circumstances the drug price schedule table may have changed from the version shown in FIG. 3, for efficiency's sake, here the drug price schedule table is treated as if it has not changed.)

In act 203, the facility determines that the number of unapplied outpatient doses, 60, is greater than or equal to the requested container size, 50; accordingly, the facility continues from act 203 to act 204. In act 204, the facility identifies the seller having the lowest 340B price among those sellers from which the requested container size has been purchased at the WAC price level. The drug price schedule 500 shown throughout in FIG. 3 contains 340B prices for Amoxicillin in rows 513, 516, and 519. The 340B price for Amoxicillin shown in row 513 for seller A, $4.90, is lower than the 340B price for Amoxicillin from the other two sellers. However, the drug purchase table 700 shown in FIG. 7 does not contain a row indicating that a 50-dose container of Amoxicillin has been purchased from seller A at the WAC price level. Accordingly, the facility selects the next—the higher 340B price, $5.20 from seller B, shown in row 560. As contrasted with seller A, the drug purchase table 700 does contain a row—row 711—indicating that a 50-dose container of Amoxicillin was purchased from seller B at the WAC price level.

After act 204, in processing the second purchase request, the facility in act 205 determines that the number of unapplied inpatient doses, 51, is greater than the container size, and thus continues in act 206. In act 206, the facility identifies as the seller with the lowest GPO price seller A, shown by row 511 of the drug price schedule table 500 to sell Amoxicillin at a price of $5.85 at the GPO price level.

For the second purchase request, in act 207, the facility selects among the following: WAC price of $11.50 from seller A; 340B price of $5.20 from seller B; and GPO price of $5.85 from seller A. In particular, the facility selects the 340B price of $5.20 from seller B.

FIG. 12 is a data structure diagram showing sample contents of the drug purchase table at a fourth time that reflect the purchase of a 50-dose container of Amoxicillin from seller B at the 340B price level in response to the second purchase request in accordance with act 209. It can be seen by comparing drug purchase table 1200 shown in FIG. 12 to drug purchase table 700 shown in FIG. 7 that the facility has added row 1213, which identifies this purchase using purchase ID 991340.

FIG. 13 is a data structure diagram showing sample contents of the dispense table at the fourth time in accordance with act 210. It can be seen by comparing dispense table 1300 shown in FIG. 13 to dispense table 1000 shown in FIG. 10 that the facility is added new purchase ID 991340 to rows 1313, 1315, and 1318 for outpatient dispenses of Amoxicillin. The facility has similarly added this new purchase ID 47 to other rows for outpatient dispenses of Amoxicillin, not shown in FIG. 13.

FIG. 14 is a data structure diagram showing sample contents of the unapplied dispense tally table to reflect the purchase in response to the second request. By comparing unapplied dispense tally table 1400 shown in FIG. 14 to unapplied dispense tally table 1100 shown in FIG. 11, it can be seen that the count of unapplied outpatient Amoxicillin dispenses has been reduced by the size of the purchase container, 50, from 60 to 10.

Those skilled in the art will appreciate that the acts shown in FIG. 2 may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

It will be appreciated by those skilled in the art that the above-described facility may be straightforwardly adapted or extended in various ways. While the foregoing description makes reference to particular embodiments, the scope of the invention is defined solely by the claims that follow and the elements recited therein.

We claim:

1. A computing system, comprising:
at least one processor; and
a memory having contents adapted to cause the computing system to, when the contents are executed by the at least one processor, perform a method, the method comprising:
    maintaining, in the memory, a first indication represented as a first row in a database table, the first indication indicating a number of doses of a distinguished drug administered by a medical institution to outpatients that have not been used as a basis for ordering the distinguished drug at a discounted outpatient price level;
    in response to each change to one or more database tables that indicate, at least in part, a current status of a plurality of drugs administered by the medical institution, causing automatic updating of the first indication by the at least one processor;
    maintaining, in the memory, a second indication represented as a second row in a database table, the second indication indicating a number of doses of the distinguished drug administered by the medical institution to inpatients that have not been used as a basis for ordering the distinguished drug at a discounted inpatient price level;
    in response to each change to the one or more database tables that indicate, at least in part, the current status of the plurality of drugs administered by the medical institution, causing automatic updating of the second indication by the at least one processor;
    in response to determining, by the at least one processor, that a distinguished quantity of the distinguished drug should be ordered on behalf of the medical institution:
        initializing, by the at least one processor, an empty set of planned orders for the distinguished drug;
        initializing, by the at least one processor, a still-needed quantity of the distinguished drug to the distinguished quantity;
        until the still-needed quantity is no larger than zero:
            determining, by the at least one processor, whether the first indication indicates a number of doses exceeding a certain quantity in which the distinguished drug is available;
            where the first indication indicates a number of doses at least as large as a certain quantity in which the distinguished drug is available, by the at least one processor performs:
                identifying, among a plurality of suppliers, a supplier offering the certain quantity of the distinguished drug at the lowest discounted outpatient price;
                adding to the set of planned orders a planned order for the certain quantity of the distinguished drug from the identified supplier at the identified supplier's discounted outpatient price;
                reducing the first indication by the certain quantity;

reducing the still-needed quantity by the certain quantity;
where (1) the first indication does not indicate a number of doses at least as large as the certain quantity and (2) the second indication indicates a number of doses at least as large as the certain quantity, by the at least one processor performs:
identifying, among the plurality of suppliers, a supplier offering the certain quantity of the distinguished drug at the lowest discounted inpatient price;
adding to the set of planned orders a planned order for the certain quantity of the distinguished drug from the identified supplier at the identified supplier's discounted inpatient price;
reducing the second indication by the certain quantity;
reducing the still-needed quantity by the certain quantity;
where (1) the first indication does not indicate a number of doses at least as large as the certain quantity and (2) the second indication does not indicate a number of doses at least as large as the certain quantity, the at least one processor performs:
identifying, among the plurality of suppliers, a supplier offering the certain quantity of the distinguished drug at the lowest undiscounted price;
adding to the set of planned orders a planned order for the certain quantity of the distinguished drug from the identified supplier at the identified supplier's undiscounted inpatient price;
reducing the still-needed quantity by the certain quantity; and
causing, by the at least one processor, the each of the planned orders of the set to be submitted to the corresponding supplier.

2. The computing system of claim 1, the method further comprising:
maintaining, in the memory, a list of administrations of the distinguished drug to outpatients that have not been used as a basis for reordering the distinguished drug at the discounted outpatient price level; and
in response to causing the orders of the set to be submitted:
for each order of the set that is at the identified supplier's discounted outpatient price, the at least one processor performs:
selecting a number of administrations from the list maintained for the distinguished drug equal to the distinguished number of doses;
for each selected administration:
storing an indication that the selected administration was used as a basis for the submitted order; and
removing the selected administration from the list maintained for the distinguished drug.

3. The computing system of claim 1 wherein the maintained indications include no more than one first indication and one second indication for each value of dispensible drug identifier.

4. The computing system of claim 1 wherein the maintained indications include no more than one first indication and one second indication for each proprietary name.

5. The computing system of claim 1 wherein the maintained indications include no more than one first indication and one second indication for each nonproprietary name.

6. The computing system of claim 1 wherein the maintained indications include no more than one first indication and one second indication for each national drug code.

7. The computing system of claim 1 wherein the maintained indications include no more than one first indication and one second indication for each national package code.

8. A computer-implemented method, comprising:
maintaining, in a memory, a first indication represented as a first row in a database table, the first indication indicating a number of doses of a distinguished drug administered by a medical institution to outpatients that have not been used as a basis for ordering the distinguished drug at a discounted outpatient price level;
in response to each change to one or more database tables that indicate, at least in part, a current status of a plurality of drugs administered by the medical institution, causing automatic updating of the first indication by at least one processor;
maintaining, in the memory, a second indication represented as a second row in a database table, the second indication indicating a number of doses of the distinguished drug administered by the medical institution to inpatients that have not been used as a basis for ordering the distinguished drug at a discounted inpatient price level;
in response to each change to the one or more database tables that indicate, at least in part, the current status of the plurality of drugs administered by the medical institution, causing automatic updating of the second indication by the at least one processor;
in response to determining, by the at least one processor, that a distinguished quantity of the distinguished drug should be ordered on behalf of the medical institution:
initializing, by the at least one processor, an empty set of planned orders for the distinguished drug;
initializing, by the at least one processor, a still-needed quantity of the distinguished drug to the distinguished quantity;
until the still-needed quantity is no larger than zero:
determining, by the at least one processor, whether the first indication indicates a number of doses exceeding a certain quantity in which the distinguished drug is available;
where the first indication indicates a number of doses at least as large as a certain quantity in which the distinguished drug is available, the at least one processor performs:
identifying, among a plurality of suppliers, a supplier offering the certain quantity of the distinguished drug at the lowest discounted outpatient price;
adding to the set of planned orders a planned order for the certain quantity of the distinguished drug from the identified supplier at the identified supplier's discounted outpatient price;
reducing the first indication by the certain quantity;
reducing the still-needed quantity by the certain quantity;
where (1) the first indication does not indicate a number of doses at least as large as the certain quantity and (2) the second indication indicates a number of doses at least as large as the certain quantity, the at least one processor performs:

identifying, among the plurality of suppliers, a supplier offering the certain quantity of the distinguished drug at the lowest discounted inpatient price;

adding to the set of planned orders a planned order for the certain quantity of the distinguished drug from the identified supplier at the identified supplier's discounted inpatient price;

reducing the second indication by the certain quantity;

reducing the still-needed quantity by the certain quantity;

where (1) the first indication does not indicate a number of doses at least as large as the certain quantity and (2) the second indication does not indicate a number of doses at least as large as the certain quantity, the at least one processor performs:

identifying, among the plurality of suppliers, a supplier offering the certain quantity of the distinguished drug at the lowest undiscounted price;

adding to the set of planned orders a planned order for the certain quantity of the distinguished drug from the identified supplier at the identified supplier's undiscounted inpatient price;

reducing the still-needed quantity by the certain quantity; and causing, by the at least one processor, the each of the planned orders of the set to be submitted to the corresponding supplier.

9. The method of claim 8, further comprising:

maintaining, in the memory, a list of administrations of the distinguished drug to outpatients that have not been used as a basis for reordering the distinguished drug at the discounted outpatient price level; and in response to causing the orders of the set to be submitted:

for each order of the set that is at the identified supplier's discounted outpatient price, the at least one processor performing:

selecting a number of administrations from the list maintained for the distinguished drug equal to the distinguished number of doses;

for each selected administration:

storing an indication that the selected administration was used as a basis for the submitted order; and removing the selected administration from the list maintained for the distinguished drug.

10. The method of claim 8 wherein the maintained indications include no more than one first indication and one second indication for each value of dispensible drug identifier.

11. The method of claim 8 wherein the maintained indications include no more than one first indication and one second indication for each proprietary name.

12. The method of claim 8 wherein the maintained indications include no more than one first indication and one second indication for each nonproprietary name.

13. The method of claim 8 wherein the maintained indications include no more than one first indication and one second indication for each national drug code.

14. The method of claim 8 wherein the maintained indications include no more than one first indication and one second indication for each national package code.

15. A non-transitory computer-readable medium storing contents that, when executed by at least one processor, cause the at least one processor to perform actions comprising:

maintaining, in a memory, a first indication represented as a first row in a database table, the first indication indicating a number of doses of a distinguished drug administered by a medical institution to outpatients that have not been used as a basis for ordering the distinguished drug at a discounted outpatient price level;

in response to each change to one or more database tables that indicate, at least in part, a current status of a plurality of drugs administered by the medical institution, causing automatic updating of the first indication;

maintaining, in the memory, a second indication represented as a second row in a database table, the second indication indicating a number of doses of the distinguished drug administered by the medical institution to inpatients that have not been used as a basis for ordering the distinguished drug at a discounted inpatient price level;

in response to each change to the one or more database tables that indicate, at least in part, the current status of the plurality of drugs administered by the medical institution, causing automatic updating of the second indication;

in response to determining, that a distinguished quantity of the distinguished drug should be ordered on behalf of the medical institution:

initializing, an empty set of planned orders for the distinguished drug;

initializing, a still-needed quantity of the distinguished drug to the distinguished quantity;

until the still-needed quantity is no larger than zero:

determining, whether the first indication indicates a number of doses exceeding a certain quantity in which the distinguished drug is available;

where the first indication indicates a number of doses at least as large as a certain quantity in which the distinguished drug is available:

identifying, among a plurality of suppliers, a supplier offering the certain quantity of the distinguished drug at the lowest discounted outpatient price;

adding to the set of planned orders a planned order for the certain quantity of the distinguished drug from the identified supplier at the identified supplier's discounted outpatient price;

reducing the first indication by the certain quantity;

reducing the still-needed quantity by the certain quantity;

where (1) the first indication does not indicate a number of doses at least as large as the certain quantity and (2) the second indication indicates a number of doses at least as large as the certain quantity:

identifying, among the plurality of suppliers, a supplier offering the certain quantity of the distinguished drug at the lowest discounted inpatient price;

adding to the set of planned orders a planned order for the certain quantity of the distinguished drug from the identified supplier at the identified supplier's discounted inpatient price;

reducing the second indication by the certain quantity;

reducing the still-needed quantity by the certain quantity;

where (1) the first indication does not indicate a number of doses at least as large as the certain quantity and (2) the second indication does not indicate a number of doses at least as large as the certain quantity:

identifying, among the plurality of suppliers, a supplier offering the certain quantity of the distinguished drug at the lowest undiscounted price;

adding to the set of planned orders a planned order for the certain quantity of the distinguished drug from the identified supplier at the identified supplier's undiscounted inpatient price;

reducing the still-needed quantity by the certain quantity; and causing the each of the planned orders of the set to be submitted to the corresponding supplier.

16. The computer-readable medium of claim 15 wherein the actions further comprise:

maintaining, in the memory, a list of administrations of the distinguished drug to outpatients that have not been used as a basis for reordering the distinguished drug at the discounted outpatient price level; and in response to causing the orders of the set to be submitted:

for each order of the set that is at the identified supplier's discounted outpatient price:

selecting a number of administrations from the list maintained for the distinguished drug equal to the distinguished number of doses;

for each selected administration:

storing an indication that the selected administration was used as a basis for the submitted order; and removing the selected administration from the list maintained for the distinguished drug.

17. The computer-readable medium of claim 15 wherein the maintained indications include no more than one first indication and one second indication for each value of dispensible drug identifier.

18. The computer-readable medium of claim 15 wherein the maintained indications include no more than one first indication and one second indication for each proprietary name.

19. The computer-readable medium of claim 15 wherein the maintained indications include no more than one first indication and one second indication for each nonproprietary name.

20. The computer-readable medium of claim 15 wherein the maintained indications include no more than one first indication and one second indication for each national drug code.

21. The computer-readable medium of claim 15 wherein the maintained indications include no more than one first indication and one second indication for each national package code.

* * * * *